United States Patent

Schmitt et al.

(10) Patent No.: US 9,763,862 B2
(45) Date of Patent: Sep. 19, 2017

(54) MULTICOMPARTMENTALIZED MATERIAL FOR THE THERMOSTIMULATED DELIVERY OF SUBSTANCES OF INTEREST, PREPARATION METHOD THEREOF AND USES OF THE SAME

(71) Applicant: CENTRE NATIONAL DE LA RECHERCHE SCIENTIFIQUE, Paris (FR)

(72) Inventors: Veronique Schmitt, Talence (FR); Maxime Nollet, Bordeaux (FR); Martin Depardieu, Orleans (FR); Renal Backov, Bordeaux-Caudera (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/409,710

(22) PCT Filed: Jun. 20, 2013

(86) PCT No.: PCT/FR2013/051439
§ 371 (c)(1),
(2) Date: Dec. 19, 2014

(87) PCT Pub. No.: WO2013/190241
PCT Pub. Date: Dec. 27, 2013

(65) Prior Publication Data
US 2015/0151267 A1    Jun. 4, 2015

(30) Foreign Application Priority Data

Jun. 21, 2012    (FR) ..................................... 12 55846

(51) Int. Cl.
*A61K 8/25*    (2006.01)
*A61K 8/37*    (2006.01)
(Continued)

(52) U.S. Cl.
CPC ................ *A61K 8/25* (2013.01); *A61K 8/025* (2013.01); *A61K 8/11* (2013.01); *A61K 8/31* (2013.01);
(Continued)

(58) Field of Classification Search
None
See application file for complete search history.

(56) References Cited

U.S. PATENT DOCUMENTS

2012/0128747 A1*  5/2012  Veronique ................ B01J 13/18
                                                                424/401

FOREIGN PATENT DOCUMENTS

WO    WO2011/012813    *  2/2011  ............. B01J 13/18

OTHER PUBLICATIONS

"Thermostimulable wax@si02 core-shell particles" Destribats et al. Dated Feb. 2, 2010.

* cited by examiner

*Primary Examiner* — Bethany Barham
*Assistant Examiner* — Barbara Frazier
(74) *Attorney, Agent, or Firm* — IPSILON USA, LLP

(57) ABSTRACT

A material in the form of solid particles with a diameter varying from 10 μm to 1 cm is provided, composed of a continuous solid shell having at least one silicon oxide, said shell imprisoning an aqueous phase The aqueous phase includes at least one hydrophilic substance of interest $S_H$ and at least one droplet of a fatty phase predominantly having a crystallizable oil in the solid state at the storage temperature of said material The crystallizable oil has a melting point ($T_M$) of less than 100° C. and including at least one lipophilic substance of interest $S_L$.

11 Claims, 2 Drawing Sheets

(51) Int. Cl.
*A61K 8/02* (2006.01)
*A61K 8/31* (2006.01)
*A61K 8/36* (2006.01)
*A61K 8/92* (2006.01)
*A61K 8/11* (2006.01)
*A61Q 15/00* (2006.01)
*A61Q 19/00* (2006.01)
*B01J 13/10* (2006.01)
*B01J 13/18* (2006.01)
*C09B 67/02* (2006.01)
*A61K 9/50* (2006.01)
*A61K 9/00* (2006.01)

(52) U.S. Cl.
CPC .............. *A61K 8/361* (2013.01); *A61K 8/375* (2013.01); *A61K 8/922* (2013.01); *A61Q 15/00* (2013.01); *A61Q 19/00* (2013.01); *B01J 13/10* (2013.01); *B01J 13/18* (2013.01); *C09B 67/0097* (2013.01); *A61K 9/0004* (2013.01); *A61K 9/501* (2013.01); *A61K 2800/412* (2013.01); *A61K 2800/56* (2013.01); *Y10T 428/2993* (2015.01)

MULTICOMPARTMENTALIZED MATERIAL FOR THE THERMOSTIMULATED DELIVERY OF SUBSTANCES OF INTEREST, PREPARATION METHOD THEREOF AND USES OF THE SAME

RELATED APPLICATIONS

This application is a National Phase Application of PCT/FR2013/051439, filed on Jun. 20, 2013, which in turn claims the benefit of priority from French Patent Application No, 12 55846 filed on Jun. 21, 2012, the entirety of which are incorporated herein by reference.

BACKGROUND

Field of the Invention

The present invention relates to a material composed of a silica shell including an aqueous phase comprising at least one droplet of crystallizable oil in the solid state, to its process of preparation, to its use for the thermostimulated delivery of active substances and to the compositions including such a material.

Description of Related Art

It may be of use to encapsulate molecules of interest, such as medicaments, dyes, pigments, reactants, fragrances, pesticides, and the like, in order to protect them from external attacks, in particular from oxidation, in order to convey them to a site of administration where they can be delivered or else in order to store them before use under conditions where they will be released from their capsule under the influence of an external stimulus. One of the first applications of microencapsulation was the development of a carbonless copy paper commercialized at the end of the 1960s, in which microcapsules imprisoning an ink were present on the back of a paper sheet so as to release the ink by rupture of the capsules under the pressure exerted by the tip of a pen during writing. At the present time, encapsulation is growing in various industrial sectors, such as pharmaceutical, cosmetics, food, textile and agricultural industries. Capsules and microcapsules are becoming increasingly sophisticated, in particular in the pharmaceutical field, where they make it possible to bring about the controlled and/or targeted delivery of active principles.

Various types and morphologies of capsules and microcapsules have already been provided, such as, for example, protein capsules, cyclodextrins, liposomes, concentrated lamellar vesicles, double emulsions, colloidosomes, microcapsules comprising silica shells, nanocapsules of silica and of heat-sensitive polymers, such as poly(N-isopropylacrylamide) (PNIPAM), heat-sensitive hydrogel microspheres, PNIPAM-Polylactide microspheres, and the like. Numerous methods which make it possible to prepare these various types of capsules and microcapsules have also been developed and perfected in recent years, such as, for example and non-exhaustively, the precipitation of polymers by phase separation, layer-by-layer electrolyte deposition, polymerization by interfacial polycondensation, and the like.

The disadvantage of the techniques already known is that the release of the molecules of interest from the capsules and microcapsules provided in the prior art is generally slow and gradual, that is to say prolonged over time.

Provision was then made to overcome this problem by providing materials composed of a silica shell including a wax core comprising one or more substances of interest, these materials being prepared by mineralization of a Pickering emulsion, that is to say of an emulsion of oil-in-water type in which the dispersion of the oil droplets in the water is stabilized by colloidal nanoparticles adsorbed at the water/oil interface (see, for example, Patent Application FR-A-2 948 581). By using a crystallizable oil to prepare these materials, that is to say an oil having a fairly low melting point ($T_M$) (for example, 37° C.), it is possible to prepare materials in which the encapsulated phase is solid under the storage conditions (for example, at ambient temperature) but becomes liquid under the conditions of use of the material (for example, at a temperature greater than 37° C. in the case of an ingestible or injectable medicament), thus bringing about the rupture of the capsule by melting and thermal expansion of the encapsulated phase and the concomitant and rapid release of the active substance or substances present in the encapsulated phase. These materials make it possible to encapsulate both lipophilic substances of interest (in the dissolved form) and hydrophilic substances of interest (in the dispersed form). However, when the encapsulated phase of these materials includes several substances of different chemical nature, these are in contact with one another, which does not make it possible, within one and the same material, to encapsulate substances which may exhibit a chemical and/or physical incompatibility. Furthermore, these materials do not make it possible to simultaneously comprise hydrophilic and lipophilic substances both in the dissolved form since only the lipophilic substances can be present in the dissolved form in the fatty phase encapsulated by the silica shell, whereas the hydrophilic substances are in the dispersed form therein.

There thus currently does not exist a compartmentalized system which makes it possible to encapsulate in the dissolved form, within one and the same material, at least two substances of interest which may furthermore possibly be incompatible with one another, said substances being lipophilic or hydrophilic, and which allows rapid and complete release of these substances of interest under the effect of an external stimulus under mild conditions.

OBJECTS AND SUMMARY

The aim of the present invention is thus to provide a material which makes it possible to encapsulate several molecules of interest in compartmentalized fashion and which also makes possible their rapid and complete release under the influence of an external stimulus and in particular of an increase in the temperature.

A subject-matter of the present invention is a material in the form of solid particles with a diameter varying from 1 µm to 1 cm which are composed of a continuous shell comprising at least one silicon oxide, said shell imprisoning an aqueous phase, said material being characterized in that said aqueous phase includes at least one hydrophilic substance of interest $S_H$ and at least one droplet of a fatty phase comprising from 50% to 99.9% by weight, with respect to the weight of said fatty phase, of a crystallizable oil in the solid state at the storage temperature of said material, said crystallizable oil having a melting point ($T_M$) of less than 100° C. and including at least one lipophilic substance of interest $S_L$.

According to the present invention, the term "storage temperature of said material" is understood to mean the temperature at which the material in accordance with the present invention is stored before it is used. This temperature is always less than the melting point of the crystallizable oil present in the fatty phase. Generally, the storage temperature corresponds to a temperature of less than or equal to ambient temperature (approximately 20° C.).

The material in accordance with the present invention exhibits the following distinguishing feature: when the material is subjected to a temperature greater than the melting point of the crystallizable oil, a thermal expansion of the fatty phase is observed, bringing about the rupture of the silica shell imprisoning the aqueous phase and the rapid and complete release of the aqueous phase comprising the hydrophilic substance or substances of interest $S_H$ and also of the molten fatty phase (that is to say, in the liquid state) comprising the lipophilic substance or substances of interest $S_L$. This result is entirely surprising in so far as the silicon oxide participating in the composition of the shell is known to be a thermal insulator. Furthermore, it was not at all obvious that the thermal expansion of the fatty phase present in the aqueous phase would make it possible to bring about the rupture of the silica shell encapsulating the aqueous phase.

In the context of this account, the term "crystallizable oil" is understood to mean fatty substances or mixtures of fatty substances, of natural (animal or vegetable) or synthetic origin, the melting point of which is greater than 15° C., the melting point of which preferably varies from 20 to 100° C. approximately and in particular from 20 to 50° C. approximately. All the melting points mentioned in the description of the present patent application refer to melting points determined by differential scanning calorimetry (DSC) at atmospheric pressure.

The crystallizable oil forms a predominant part of the fatty phase and can even, apart from the substance or substances of interest $S_L$ which it includes, be the only constituent of the fatty phase. The crystallizable oil preferably represents from 75% to 99.9% by weight approximately, with respect to the weight of the fatty phase.

The choice of the crystallizable oil naturally depends on the application envisaged for the material and thus on the temperature at which it is desired to observe the thermal expansion of the fatty phase and consequently the rupture of the silica shell encapsulating the aqueous phase. Mention may in particular be made, among the crystallizable oils which can be used according to the invention, of paraffin waxes, such as the paraffin waxes having a melting point between 42 and 44° C. or between 46 and 48° C. [RN-8002-74-2] sold by Merck, triglycerides, fatty acids, rosins, waxes (long alkanes), such as icosane and octadecane, hydrogenated vegetable oils and their mixtures, and synthetic bitumens. These oils can be used alone or as mixtures.

The material in accordance with the present invention is preferably provided in the form of a powder of spherical or substantially spherical particles.

The diameter of the particles preferably varies from 5 μm to 500 μm approximately and more preferably still from 10 μm to 200 μm.

The diameter of the droplet or droplets of fatty phase present in each particle of the material in accordance with the invention generally varies from 8 μm to 80 μm and preferably from 30 μm to 70 μm.

According to a preferred embodiment of the invention, each particle of material in accordance with the invention comprises only a single droplet of fatty phase in the aqueous phase present in the silica shell and the volume of said droplet of fatty phase represents from 30% to 70% of the internal volume of the particles.

The silica shell must have a thickness sufficient to have a mechanical strength which makes possible the encapsulation of the aqueous phase. However, it must also exhibit a thickness which allows it to burst during a rise in the temperature to a temperature greater than the melting point of the fatty phase present in the aqueous phase. The thickness of the silica shell generally varies from 0.1 to 2 μm approximately and preferably from 0.2 to 2 μm approximately.

In addition to the silicon oxide, the silica shell can additionally comprise one or more metal oxides of formula $MeO_2$ in which Me is a metal chosen from Zr, Ti, Th, Nb, Ta, V, W and Al. In this case, the silica shell is composed of a mixed matrix of $SiO_2$-$MeO_2$ type in which the content of $MeO_2$ remains minor with respect to the content of silicon oxide; preferably, the content of $MeO_2$ represents from 1% to 40% by weight, more particularly from 5% to 30% by weight, with respect to the total weight of the shell.

Mention may in particular be made, among the substances of interest which can be incorporated in the aqueous phase and in the fatty phase present in the aqueous phase of the material in accordance with the present invention, of medicaments (active principles), active principles which can be used in cosmetics, chemical reactants, dyes, pigments, inks, and the like. Of course, these substances are incorporated in the fatty phase present in the aqueous phase when they are lipophilic and in the aqueous phase when they are hydrophilic, a person skilled in the art knowing how to distinguish the lipophilic or hydrophilic nature of a given substance as a function of its HLB ("Hydrophilic-Lipophilic Balance") value.

Mention may be made, as examples of medicaments, of bactericides, such as antiseptics and antibiotics, anti-inflammatories, analgesics, local laxatives, hormones, proteins, and the like.

Mention may in particular be made, as examples of cosmetic active principles, of vitamins, sunscreens, antioxidants, such as agents for combating free radicals, for example superoxide dismutase, fragrances, odour absorbers, deodorant agents, antiperspirant agents, dyes, pigments, emollients, moisturizing agents, and the like.

Mention may in particular be made, as examples of chemical reactants, of coloured reactants, coloured indicators, such as pH indicators, catalysts, polymerization initiators, monomers, complexing agents, and the like.

The substance or substances of interest $S_L$ generally represent from 0.001% to 50% by weight approximately and preferably from 0.01% to 25% by weight approximately of the weight of the fatty phase present in the aqueous phase.

The substance or substances of interest $S_H$ generally represent from 0.1% to 50% by weight approximately and preferably from 0.1% to 25% by weight approximately of the weight of the aqueous phase.

The aqueous phase and/or the fatty phase present in the aqueous phase can, in addition, include one or more additives conventionally used in emulsions and among which may in particular be mentioned, by way of example, agents for protecting or preserving the substance of interest, such as antioxidants, UV inhibitors, and the like.

Another subject-matter of the invention is a process for the preparation of the material as defined above. This process is characterized in that it comprises the following stages, consisting:

1) in a first stage, in bringing a first fatty phase FP1 comprising from 50% to 99.9% by weight, with respect to the weight of said fatty phase FP1, of a solid crystallizable oil (CO) having a melting point $T_M$ of less than 100° C. to a temperature $T_{CO}$ such that $T_{CO}$ is greater than $T_M$, in order to obtain a fatty phase FP1 in the liquid state;

2) in a second stage, in incorporating, in the fatty phase FP1 in the liquid state, at least one lipophilic substance of interest ($S_1$);

3) in a third stage, in bringing said fatty phase FP1 in the liquid state into contact with an aqueous phase (AP) brought beforehand to a temperature $T_{AP}$ such that $T_{AP}$ is greater than $T_M$, said aqueous phase additionally including at least one hydrophilic substance of interest ($S_H$) and solid colloidal particles;

4) in a fourth stage and still at a temperature of greater than $T_M$, in subjecting the liquid mixture resulting from the third stage to mechanical stirring in order to obtain an oil-in-water (O/W) emulsion formed of droplets of fatty phase FP1 in the liquid state dispersed in the continuous aqueous phase and in which the solid colloidal particles are present at the interface formed between the continuous aqueous phase and the dispersed droplets of fatty phase FP1;

5) in a fifth stage and still at a temperature of greater than $T_M$, in adjusting the pH of the O/W emulsion obtained above in the preceding stage to a value of less than or equal to 1 using an acidifying agent;

6) in a sixth stage and still at a temperature of greater than $T_M$, in adding the O/W emulsion obtained above in the preceding stage to a fatty phase FP2 comprising an oil which is liquid at the temperature $T_{O/W}$ and additionally including at least one non-ionic surfactant and at least one silicon oxide precursor;

7) in a seventh stage and still at a temperature of greater than $T_M$, in subjecting the mixture resulting from the sixth stage to mechanical stirring in order to obtain an oil-in-water-in-oil (O/W/O) double emulsion formed of a continuous oily phase (FP2) including droplets of aqueous phase AP, each of said droplets of aqueous phase including at least one droplet of fatty phase FP1 in the liquid state;

8) in an eighth stage, in allowing the O/W/O double emulsion obtained above in the preceding stage to return to a temperature $T_{O/W/O}$ of less than $T_M$, without stirring, in order to bring about, on the one hand, the solidification of the fatty phase FP1 and, on the other hand, the formation of a silicon oxide shell around said droplets of aqueous phase AP (mineralization of the emulsion) and to thus obtain the expected material;

9) in a ninth stage, in separating said material from the fatty phase FP2.

The crystallizable oil used during the first stage and also the lipophilic and hydrophilic substances of interest mentioned in stages 2) and 3) respectively are as defined above with reference to the material in accordance with the invention.

The solid colloidal particles present in the aqueous phase used during the third stage can be inorganic or organic. Preferably, they are inorganic particles chosen from the group of metal oxides, hydroxides and sulphates. Mention may very particularly be made, among such oxides, of oxides of silicon, titanium, zirconium and iron, and also their salts, such as silicates (for example clays). Finally, mention may be made of colloidal carbon particles. Mention may in particular be made, among solid organic colloidal particles, of polymeric particles, for example latex particles.

In order to be colloidal, the solid particles generally exhibit a size of less than a few micrometers. Thus, these particles generally exhibit a mean size of between 5 and 5000 nm and preferably between 5 and 500 nm.

According to a particularly preferred embodiment of the invention, the solid colloidal particles are chosen from silicon oxide nanoparticles. Mention may in particular be made, by way of example, of the products sold under the Aerosil® trade name by Evonik Degussa.

The amount of solid colloidal particles generally varies from 0.01% to 10%, in particular from 0.1% to 7% and preferably from 1% to 5% by weight approximately, with respect to the total weight of the aqueous phase AP.

Advantageously, the amount of solid colloidal particles present in the aqueous phase varies as a function of the mean size by volume of the droplets of fatty phase FP1 desired in the emulsion, the mean diameter of which varies from 10 to 100 µm, preferably from 10 to 30 µm and more preferably still from 15 to 25 µm approximately.

Furthermore, the solid colloidal particles generally exhibit a hydrophilic and charged surface which does not promote their adsorption at the surface of the droplets of the fatty phase FP1.

Thus, and according to a preferred embodiment of the invention, the solid colloidal particles are functionalized at the surface in order to promote their adsorption at the interface formed between the fatty phase FP1 and the continuous aqueous phase AP during stage 4).

The solid colloidal particles can thus be functionalized by compounds bonded to their surface via covalent bonds. This can be carried out by prior treatment of the particles, in particular by chemical grafting of a compound comprising hydrophobic groups, such as a trialkoxysilane of formula R—Si—(OR')$_3$, in which R is a linear or branched $C_1$ to $C_{12}$ alkyl, in particular from $C_2$ to $C_{10}$, very particularly n-octyl, optionally carrying an amino group, and R', which is identical to or different from R, is a linear or branched $C_1$ to $C_{12}$ alkyl group, in particular from $C_1$ to $C_6$, and very particularly ethyl.

The solid colloidal particles can also be functionalized by adsorption of surfactant molecules at their surface which makes it possible to confer on them a degree of hydrophobicity, the hydrophilic end of the surfactant being adsorbed on the surface of the particles. The surfactants which can be used to functionalize the particles are preferably cationic or anionic surfactants.

Preference is given, among these surfactants, in particular to sodium alkyl sulphates, such as, in particular, sodium dodecyl sulphate (SDS), and alkyltrimethylammonium bromides.

The surfactant is preferably chosen from surfactants having an opposite charge to that of the surface of the solid colloidal particles. This choice makes it possible to promote the adsorption of the surfactant at the surface of the particles.

Mention may in particular be made, as example of particles functionalized by a surfactant, of silica nanoparticles, the surface of which is functionalized by a quaternary ammonium, such as those sold under the name Aerosil® A380 by Evonik Degussa, with a diameter of 7 nm, the surface of which is functionalized by cetyltrimethylammonium bromide (CTAB).

The functionalization of the solid colloidal particles by a surfactant can also be carried out in situ, that is to say during their introduction into the aqueous phase AP of the emulsion. In this case, the aqueous phase AP of the emulsion additionally includes said surfactant in an amount preferably below the critical micelle concentration (CMC), the surfactant then being adsorbed at the surface of the particles when the latter are in the aqueous phase of the emulsion. Preferably, the amount of surfactant varies from $1/200^{th}$ to $1/2$ of the CMC.

The aqueous phase comprises mainly water and optionally an alcohol, such as methanol, ethanol, isopropanol or butanol, preferably ethanol.

According to a preferred embodiment of the invention, the amount of fatty phase FP1 used during the third stage represents at most 40% by weight approximately and more preferably still from 30% to 40% by weight approximately, with respect to the weight of the aqueous phase.

The mechanical stirring operations carried out during the fourth and seventh stages can in particular be carried out in a device intended to emulsify, such as, for example, in devices sold under the Ultra-Turrax® or Rayneri® trade names.

The size distribution of the droplets of fatty phase FP1 in the O/W emulsion is generally narrow (U<40%).

The pH of the aqueous phase during the fifth stage is preferably adjusted to a value varying from −0.5 to 0.5 and more preferably still from −0.25 to 0.

The acidifying agent used to adjust the pH of the aqueous phase can be chosen from inorganic and organic acids, among which may in particular be mentioned hydrochloric acid, acetic acid, nitric acid and sulphuric acid.

The oil which is liquid at the temperature $T_{O/W}$ used as fatty phase FP2 during the sixth stage can, for example, be chosen from polydimethylsiloxanes, peanut oil, sunflower oil, triesters, and the like, and their mixtures.

A person skilled in the art will take care to preferably choose an oil which is a liquid at the temperature $T_{O/W}$, the use of which is compatible with the process in accordance with the invention, that is to say a liquid oil in which the crystallizable oil used as fatty phase FP1 is not soluble.

The non-ionic surfactant also used during the sixth stage makes it possible to stabilize the double emulsion, that is to say the dispersion of the droplets of aqueous phase within the fatty phase FP2. The nature of the non-ionic surfactant is not critical, as long as it is soluble in the fatty phase FP2. According to a preferred embodiment of the invention, the non-ionic surfactant is chosen from cyclic polydimethylsiloxanes, ethoxylated block copolymers, nonylphenols, and their mixtures.

Also according to a preferred embodiment of the invention, the non-ionic surfactant represents from 1% to 5% by weight approximately and more preferably still from 2% to 4% by weight approximately, with respect to the total weight of the fatty phase FP2.

According to a preferred embodiment of the invention, during the sixth stage, the O/W emulsion represents at most 20% by weight and more preferably still at most 10% by weight approximately of the weight of the fatty phase FP2.

The silicon oxide precursors used during the sixth stage can be chosen from silicon alkoxides and in particular from tetramethoxyorthosilane (TMOS), tetraethoxyorthosilane (TEOS), dimethyldiethoxysilane (DMDES), (3-mercaptopropyl)trimethoxysilane, (3-aminopropyl)triethoxysilane, N-(3-trimethoxysilylpropyl)pyrrole, 3-(2,4-dinitrophenylamino)propyltriethoxysilane, N-(2-aminoethyl)-3-aminopropyltrimethoxysilane, phenyltriethoxysilane, methyltriethoxysilane and their mixtures. Among these precursors, TEOS is particularly preferred. These precursors can be completely or partially replaced by silicate sols.

The thickness of the shell formed around each droplet of aqueous phase depends on the amount of silicon oxide precursors used during the sixth stage and on the diameter of the droplets of the aqueous phase dispersed in the fatty phase FP2.

According to a preferred embodiment of the invention, the amount of silicon oxide precursor varies from 1% to 7% by weight approximately and more particularly from 3% to 5% by weight approximately, with respect to the total weight of the double emulsion.

In order to achieve greater shell thicknesses, it is possible to add additional amounts of silicon oxide precursor during the course of stage 8).

When the silica shells of the material in accordance with the invention comprise a metal oxide in addition to the silicon oxide, at least one precursor of a metal oxide of formula $MeO_2$ is then also added to the aqueous phase of the double emulsion, said precursor being chosen from the alkoxides, chlorides or nitrates of the metals chosen from Zr, Ti, Th, Nb, Ta, V, W and Al.

When they are used, the amount of these precursors of metal oxide of formula $MeO_2$ varies from 1% to 7% approximately and more particularly from 3% to 5% by weight approximately, with respect to the total weight of the double emulsion.

During the eighth stage (mineralization of the emulsion), the acid pH conditions bring about the hydrolysis and the condensation of the silicon oxide precursor or precursors at the interface of the droplets of aqueous phase dispersed in the fatty phase FP2. There is thus formation of a silica shell around each of the droplets of aqueous phase AP present in the fatty phase FP2.

During the ninth stage, the material in accordance with the invention can be separated from the fatty phase FP2 and recovered by any conventional separation technique known to a person skilled in the art, such as filtration, centrifuging and the use of sieves. It is subsequently preferably washed, for example with water or employing the oil used in the fatty phase FP2 during its preparation, and then dried, for example by freeze drying, to give a powder.

The material thus obtained is stable on storage for several months provided that the storage temperature is less than the melting point $T_M$ of the fatty phase FP1 present in the aqueous phase imprisoned in the silica shell.

The material in accordance with the invention can be used in the powder form or in the form of a dispersion in a solvent in order to deliver the lipophilic substance or substances of interest present in the solid fatty phase FP1 present in the aqueous phase imprisoned in the silica-based shell and also the hydrophilic substance or substances of interest present in the aqueous phase.

Another subject-matter of the invention is thus the use of a material in accordance with the invention and as described above for the thermostimulated and simultaneous delivery of at least one lipophilic substance of interest and of at least one hydrophilic substance of interest.

The delivery of the lipophilic and hydrophilic substances of interest is obtained by thermal expansion of the fatty phase FP1 present in the aqueous phase, bringing about the rupture of the silica shell surrounding the aqueous phase, under the effect of a rise in the temperature of the material to a delivery temperature $T_D$ such that $T_D > T_M$.

By way of example and when the substances of interest are lipophilic and hydrophilic active principles having a medicinal action or food supplement active ingredients, such as, for example, lipophilic and hydrophilic vitamins, the crystallizable oil present in the fatty phase is preferably chosen from crystallizable oils having a melting point of less than 37° C. Thus, when said material is incorporated in a pharmaceutical composition and when this composition is administered to a patient, for example orally, the composition ingested will be at body temperature, generally 37° C. or more, which will result in the melting of the fatty phase and in its expansion in volume and thus the rupture of the silica shell surrounding the aqueous phase and the delivery of the active principles or of the active ingredients.

According to another example, the lipophilic and hydrophilic substances of interest are cosmetic active principles and the material is one of the components of a cosmetic composition for topical application, such as a powder, a cream or a gel. The heating of the fatty phase of the material to a temperature greater than $T_M$ can in this case be brought about by local rubbing during the spreading of the cosmetic composition, which causes local heating bringing about the rupture of the silica shells and the local release of the substances of interest. If the cosmetic composition is provided in the form of a powder, its application by spreading can be accompanied by a change in texture (transformation of the powder into a composition having a greasy feel due to the rupture of the shell).

Mention may in particular be made, as other examples of the use of the material in accordance with the invention, of:
the use for the simultaneous delivery of lipophilic and hydrophilic initiators of a polymerization reaction brought about by a rise in the temperature; in this case, the material in accordance with the invention can, for example, be used for the manufacture of solid foams in the field of insulating materials.

Another subject-matter of the invention is the use of the material as described above as ingredient for the preparation of pharmaceutical, cosmetic or food products and also the pharmaceutical, cosmetic or food products including, as ingredient, at least one material in accordance with the invention.

These compositions can include conventional pharmaceutical, cosmetic or food vehicles well known to a person skilled in the art and also one or more surfactants intended to promote the release of the liquid fatty phase and of the encapsulated aqueous phase during the rupture of the silica shell.

DETAILED DESCRIPTION

Figure 1:
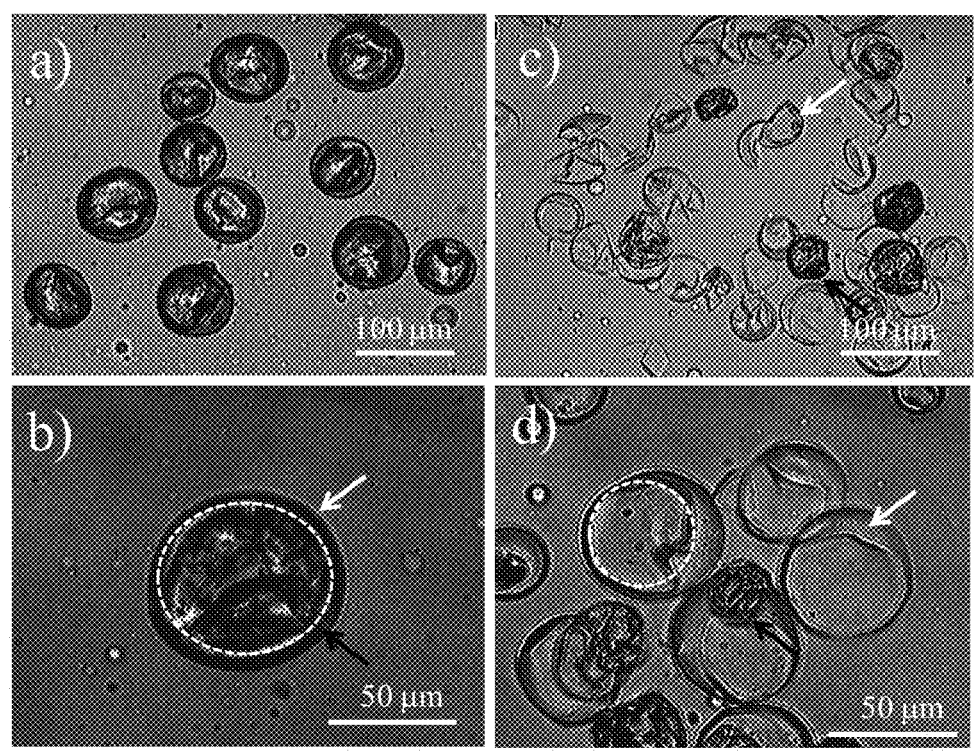
FIGS. 1a-1d are optical microscopy photographs of the particles of the final material in accordance with one embodiment.

The present invention is illustrated by the following implementational examples, to which, however, it is not limited.

EXAMPLES

The starting materials used in the examples which follow are listed below:
Paraffin 42-44 in block form, having a melting range from 42 to 44° C. (CAS No. 8002-74-2), sold by Merck; the expansion in volume of this fatty phase on changing its temperature from ambient temperature to 55° C. is approximately 13%;
Tetraethoxyorthosilane, more than 99% pure (TEOS);
Rhodamine B: Sigma-Aldrich;
Cetyltrimethylammonium bromide (CTAB): ChemPur;
Cyclic polydimethylsiloxanes, sold under the trade name DC3225C by Dow Corning (non-ionic surfactant);
Silica nanoparticles with a diameter of 7 nm, sold under the name Aerosil® A380: Evonik Degussa;
Hydrochloric acid, 37% by volume (Carlo Erba Reagents);
PDMS DC200, viscosity 200 cSt: Aldrich.
These starting materials were used as received from the manufacturers, without additional purification.

The critical micelle concentration (CMC) of the CTAB in pure water at ambient temperature is 0.92 mM.

The materials obtained were characterized using an inverted optical microscope sold under the trade name Axiovert® X100 by Zeiss and equipped with a heating stage from Mettler which makes it possible to control the temperature and also the heating and cooling rates.

The size distribution of the emulsions was studied using a particle sizer sold under the trade name Mastersizer Hydro MS2000 by Malvern Instrument. The particle size measurements were carried out at 25° C. in pure water. The intensity of the scattering as a function of the angle which was collected was converted using the Mie-Lorenz theory. The distribution in the size of the particles was expressed by their weighted mean diameter (D) and their polydispersity (P) by applying the following equations (1) and (2):

$$D = \frac{\sum_i N_i D_i^3}{\sum_i N_i D_i^2} \tag{1}$$

and $$P = \frac{1}{\overline{D}} \frac{\sum_i N_i D_i^3 |\overline{D} - D_i|}{\sum_i N_i D_i^3} \tag{2}$$

in which:
$D_i$ is the diameter of the particles,
$N_i$ is the total number of droplets with the diameter $D_i$,
$\overline{D}$ is the median diameter, that is to say the theoretical opening of the sieve such that 50% of the particles, by weight, have a greater diameter and 50% have a smaller diameter.

These formulae are applied in the particle sizers from Malvern Instrument.

Example 1: Preparation, Characterizations and Study of a Material in Accordance with the Invention In this example, the preparation, the characterization and the study of a material in accordance with the invention, composed of a silica shell including an aqueous phase comprising a fatty phase in the form of a droplet of crystallizable oil, are illustrated.

It should be noted that, in this example, the fatty and aqueous phases do not include substances of interest, this example being given to demonstrate the structural feasibility of the compartmentalized material according to the process in accordance with the invention.

It is easy to extrapolate the process below to fatty and aqueous phases respectively including at least one lipophilic substance of interest and at least one hydrophilic substance of interest, their use not in any way modifying the process in accordance with invention or the structure of the material obtained.

1) Preparation of the Material
   i): Functionalization of the Silica Particles
   72 mg of Aerosil® A380 silica nanoparticles were dispersed in 7 ml of distilled water using an ultrasonic bath. 0.66 mg of CTAB/g of particles were subsequently added to this dispersion, this amount representing approximately ⅕ of the critical micelle concentration (CMC=0.92 mM). As the surface of the silica nanoparticles is negatively charged, the CTAB (cationic surfactant) is adsorbed at the surface of the silica particles and thus makes it possible to confer on them an amphiphilic nature. An aqueous phase including a dispersion of silica nanoparticles functionalized at the surface was obtained.

The amount of CTAB was adjusted to the weight of the silica particles in order to obtain a specific coverage of 25 nm²/CTAB molecule at the silica/water interface, all the CTAB used being regarded as adsorbed at the surface of the silica particles.

ii) Preparation of the O/W Emulsion 3 g of paraffin wax were added to a receptacle containing 7 g of water including 72 mg of silica particles as functionalized above in i).

The receptacle was brought to a temperature of 60° C. in order to bring about the melting of the paraffin wax (fatty phase).

The emulsification of the fatty phase and of the aqueous phase was carried out using a stirrer sold under the name Ultra-Turrax® T25 by Janke & Kunkel, equipped with an S25 KV-25F dispersing device, at 9000 revolutions/min for 30 seconds. The resulting monodisperse O/W emulsion thus obtained (mean size of the droplets of fatty phase centred at a diameter of 20 μm) was maintained at 60° C. in a thermostatically controlled bath without stirring in order to allow the phenomenon of limited coalescence to occur (adsorption of the silica particles at the surface of the dispersed droplets of fatty phase, which makes it possible to improve the homogeneity of the distribution in the size of the oil droplets dispersed in the water).

iii) Preparation of the O/W/O Emulsion

The pH of the continuous aqueous phase of the O/W emulsion obtained above in the preceding stage was subsequently adjusted to a value of approximately 0 by addition of hydrochloric acid. This very low pH value subsequently makes it possible to catalyse the hydrolysis of the TEOS and its condensation in the form of silicon oxide at the FP2/AP interface.

0.8 g of the O/W emulsion thus acidified was subsequently added to a fatty phase FP2 containing 8.2 g of PDMS, 0.3 g of DC3225C surfactant and 0.5 g of TEOS.

The emulsification of the O/W emulsion in the fatty phase FP2 was carried out using the same stirrer as above in stage ii), finishing by stirring at 3500 revolutions/min for 10 seconds. The O/W/O double emulsion thus obtained was subsequently stored at ambient temperature without stirring for 24 hours in order to bring about the solidification of the fatty phase and to allow the hydrolysis of the TEOS and its condensation in the form of a silica shell to occur around the droplets of aqueous phase.

After 24 hours, the material obtained and sedimented at the bottom of the receptacle was recovered and dispersed again in PDMS in order to remove any residue of non-encapsulated crystallizable oil and any droplet of aqueous phase also non-encapsulated or not containing encapsulated fatty phase.

2) Results and Characterizations

The appended FIG. 1 represents an optical microscopy photograph of the particles of the final material thus obtained: FIG. 1a is a view of several particles after sedimentation, FIG. 1b is centred on a single particle and FIGS. 1c and 1d show the particles of the material after application of a mechanical pressure using a spatula at ambient temperature to the slide covering the drop observed with the microscope, this mechanical pressure having brought about the rupture of the silica shells. In these figures, the white arrows mark off the silica shells, the black arrows mark off the droplets of solid fatty phase after rupture of the shell and the white circles in dotted lines show that the space reserved for the fatty phase is filled with a fatty phase in FIG. 1b whereas it is empty of fatty phase after rupture of the silica shell in FIG. 1d.

It was subsequently confirmed that an increase in the temperature brought about the rupture of the silica shells and the release of the aqueous phase and of the molten fatty phase.

Figure 2:
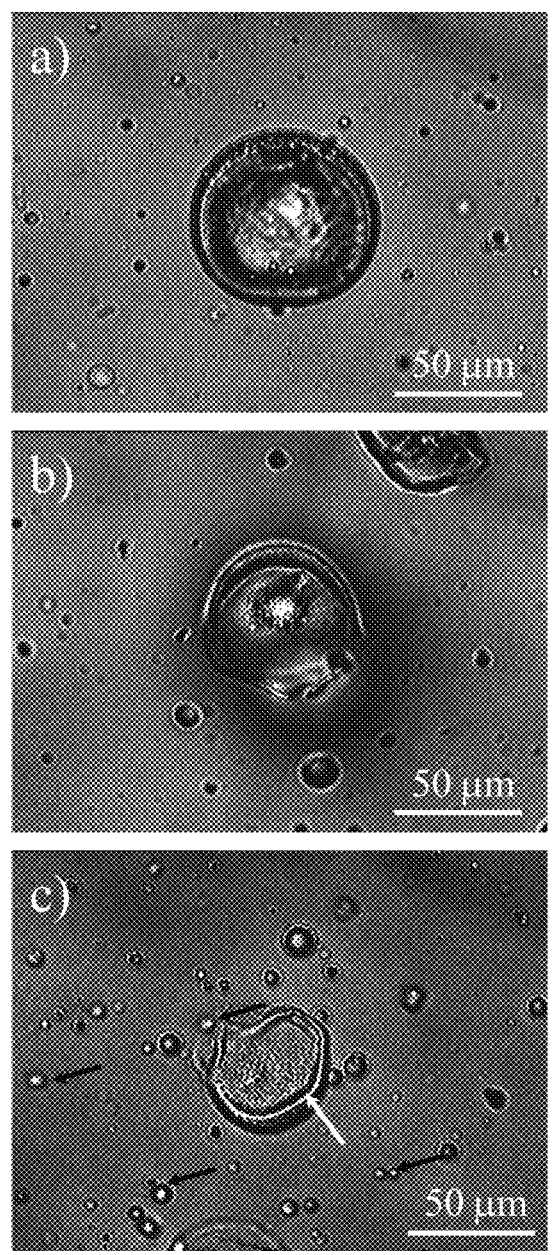
FIGS. 2a-2c are confocal microscopy images taken of the material before and after raising the temperature in accordance with one embodiment.

The material was incorporated in an oily phase composed of PDMS and including 20% by weight of DC3225C. The composition obtained was brought to a temperature of 44° C. by gradually raising the temperature at the rate of 5° C. per minute on the heating stage of the microscope. The composition was observed in confocal microscopy before and after raising the temperature. The corresponding photos are given in the appended FIG. 2. In this figure, FIG. 2a corresponds to the image taken before raising the temperature, whereas FIGS. 2b and 2c correspond to images taken after raising the temperature. It is found that raising the temperature brings about the melting of the fatty phase present in the aqueous phase, the rupture of the silica shell (white arrow in FIG. 2c) and the expulsion of the molten fatty phase into the oily phase (PDMS) of the composition, where it dissolves, and also the expulsion of the aqueous phase in the form of a few droplets (black arrows).

It is thus possible to simultaneously release lipophilic and hydrophilic substances which would be respectively present in the fatty phase and in the aqueous phase AP by simple raising of the temperature of the materials in accordance with the invention.

The invention claimed is:

1. Material in the form of solid particles with a diameter varying from 10 μm to 1 cm which are composed of a continuous solid shell comprising:
at least one silicon oxide, said shell imprisoning an aqueous phase, wherein said aqueous phase includes at least one hydrophilic substance of interest $S_H$ and at least one droplet of a fatty phase comprising from 50% to 99.9% by weight, with respect to the weight of said fatty phase, of a crystallizable oil in the solid state at the storage temperature of said material, said crystallizable oil having a melting point ($T_M$) of less than 100° C. and including at least one lipophilic substance of interest $S_L$, wherein said substances of interest are selected from the group consisting of antiseptics, antibiotics, anti-inflammatories, local laxatives, hormones, proteins, vitamins, sunscreens, antioxidants, agents for combating free radicals, superoxide dismutase, fragrances, odor absorbers, deodorant agents, antiperspirant agents, dyes, pigments, emollients, moisturizing agents, pH indicators, catalysts, polymerization initiators, monomers, and complexing agents.

2. Material according to claim 1, wherein the crystallizable oil is chosen from fatty substances and mixtures of fatty substances, of natural or synthetic origin, the melting point of which is greater than 15° C. and less than 100° C.

3. Material according to claim 1, wherein the crystallizable oil is a paraffin wax.

4. Material according to claim 1, wherein said material is provided in the form of a powder of spherical or substantially spherical particles.

5. Material according to claim 1, wherein the diameter of the droplet or droplets of fatty phase present in each particle of the material varies from 8 μm to 80 μm.

6. Material according to claim 1, wherein each particle of material comprises only a single droplet of fatty phase in the aqueous phase present in the silica shell and the volume of said droplet of fatty phase represents from 30% to 70% of the internal volume of the particles.

7. Material according to claim 1, wherein the silica shell has a thickness of 0.1 to 2 μm.

8. Material according to claim 1, wherein the silica shell additionally comprises one or more metal oxides of the formula $ZrO_2$.

9. Material according to claim 1, wherein the substance or substances of interest $S_L$ represent from 0.001% to 50% by weight of the total weight of the fatty phase present in the aqueous phase.

10. Material according to claim 1, wherein the substance or substances of interest $S_H$ represent from 0.001% to 50% by weight of the weight of the aqueous phase.

11. Pharmaceutical, cosmetic or food products, wherein they include, as ingredient, at least one material as defined in claim 1.

* * * * *